United States Patent
Nirogi et al.

(10) Patent No.: US 10,005,711 B2
(45) Date of Patent: Jun. 26, 2018

(54) PROCESS FOR LARGE SCALE PRODUCTION OF 1-ISOPROPYL-3-{5-[1-(3-METHOXYPROPYL)PIPERIDIN-4-YL]-[1,3,4]OXADIAZOL-2-YL}-1H-INDAZOLE OXALATE

(71) Applicant: SUVEN LIFE SCIENCES LIMITED, Hyderabad, Andhra Pradesh (IN)

(72) Inventors: Ramakrishna Nirogi, Hyderabad (IN); Abdul Rasheed Mohammed, Hyderabad (IN); Venkateswarlu Jasti, Hyderabad (IN)

(73) Assignee: SUVEN LIFE SCIENCES LIMITED, Hyderabad, Andhra (IN)

( * ) Notice: Subject to any disclaimer, the term of this patent is extended or adjusted under 35 U.S.C. 154(b) by 0 days. days.

(21) Appl. No.: 15/504,224

(22) PCT Filed: Oct. 23, 2014

(86) PCT No.: PCT/IN2014/000677
§ 371 (c)(1),
(2) Date: Feb. 15, 2017

(87) PCT Pub. No.: WO2016/027277
PCT Pub. Date: Feb. 25, 2016

(65) Prior Publication Data
US 2017/0283359 A1   Oct. 5, 2017

(30) Foreign Application Priority Data
Aug. 16, 2014   (IN) .......................... 4009/CHE/2014

(51) Int. Cl.
| | | |
|---|---|---|
| *C07D 413/14* | (2006.01) | |
| *C07C 51/43* | (2006.01) | |
| *C07C 55/07* | (2006.01) | |
| *C07C 51/41* | (2006.01) | |

(52) U.S. Cl.
CPC ............ *C07C 51/412* (2013.01); *C07C 51/43* (2013.01); *C07C 55/07* (2013.01); *C07D 413/14* (2013.01)

(58) Field of Classification Search
CPC ...... C07D 413/14; C07C 51/412; C07C 51/43
USPC .................................................... 546/275.7
See application file for complete search history.

(56) References Cited

U.S. PATENT DOCUMENTS

| 7,419,989 B2 * | 9/2008 | Fatheree | C07D 451/04 514/304 |
| 8,044,045 B2 * | 10/2011 | Marquess | C07D 451/04 514/228.2 |
| 9,079,894 B2 * | 7/2015 | Nirogi | C07D 413/14 |
| 2006/0135764 A1 * | 6/2006 | Fatheree | C07D 451/04 544/60 |

FOREIGN PATENT DOCUMENTS

| EP | 0839791 | * | 6/1998 | |
| WO | WO-2005080389 A1 | * | 9/2005 | ........... C07D 451/04 |
| WO | 2013042135 A1 | | 3/2013 | |
| WO | 2015092804 A1 | | 6/2015 | |

OTHER PUBLICATIONS

Ibrahim Sakka 2005. Synthetic uses of thionyl chloride.*
El-Sakka Ibrahim 2005 Synthetic use of Thionyl Chloride.*
European Patent Office, "International Search Report" and "Written Opinion of International Search Authority", PCT Application No. PCT/IN2014/000677 dated Mar. 25, 2015.
European Patent Office, "Written Opinion of International Preliminary Examination Authority", PCT Application No. PCT/IN2014/000677 dated Aug. 16, 2016.
Response to Written Opinion of International Search Authority, PCT Application No. PCT/IN2014/000677, dated Feb. 15, 2016.
Revised Response to Written Opinion of International Search Authority, PCT Application No. PCT/IN2014/000677, dated Feb. 16, 2016.
Response to Written Opinion of International Preliminary Examination Authority, PCT Application No. PCT/IN2014/000677, dated Oct. 7, 2016.
European Patent Office, "International Preliminary Report on Patentability", PCT Application No. PCT/IN2014/000677 dated Nov. 4, 2016.
Oades, "Role of the serotonin system in ADHD: treatment implications." Expert Review of Neurotherapeutics, 7 (10):1357-74 (2007).
Cho and Hu, "Activation of 5-HT4 receptors inhibits secretion of b-amyloid peptides and increases neuronal survival" Experimental Neurology 203(1):274-78 (2007).
Ahmad and Nirogi, "5-HT4 receptor agonists for the treatment of Alzheimer's disease" Neuroscience & Medicine 2:87-92 (2011).
Gray and Roth, "Molecular targets for treating cognitive dysfunction in schizophrenia" Schizophrenia Bulletin 33(5):1100-1119 (2007).

* cited by examiner

Primary Examiner — Rita J Desai
(74) Attorney, Agent, or Firm — IPHorgan Ltd.

(57) ABSTRACT

The present invention relates to a process suitable for adoption to large scale manufacture of 1-isopropyl-3-{5-[1-(3-methoxypropyl)piperidin-4-yl]-[1,3,4]oxadiazol-2-yl}-1H-indazole oxalate of formula (I), which is a selective 5-$HT_4$ receptor ligand intended for the symptomatic treatment of Alzheimer's disease and other disorders of memory and cognition like Attention deficit hyperactivity, Parkinson's and Schizophrenia.

14 Claims, No Drawings

PROCESS FOR LARGE SCALE PRODUCTION OF 1-ISOPROPYL-3-{5-[1-(3-METHOXYPROPYL)PIPERIDIN-4-YL]-[1,3,4]OXADIAZOL-2-YL}-1H-INDAZOLE OXALATE

CROSS REFERENCE TO RELATED APPLICATIONS

This application is a national stage completion application of PCT Application No. PCT/IN2014/000677, filed Oct. 23, 2014, and claims the benefit of India Application No. 4009/CHE/2014, filed Aug. 16, 2014. Each of these applications is incorporated by reference herein in its entirety.

FIELD OF THE INVENTION

The present invention comprises of process for the synthesis of 1-Isopropyl-3-{5-[1-(3-methoxypropyl) piperidin-4-yl]-[1,3,4]oxadiazol-2-yl}-1H-indazole oxalate of formula (I), which is suitable for adoption to large scale manufacturing.

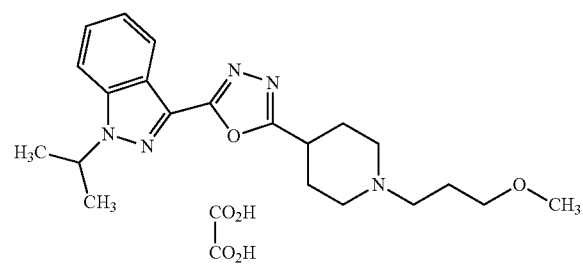

(I)

BACKGROUND OF THE INVENTION

Alzheimer's disease (AD) is a neurodegenerative disorder of advanced age characterized by loss of memory, accumulation of amyloid beta protein (Aβ) deposits and decreased levels of the neurotransmitter acetylcholine. Approximately forty percent of AD patients suffer from significant depression. 5-HT4 receptor partial agonists may be of benefit for both the symptomatic and disease-modifying treatment for AD and may offer improved clinical efficacy and/or tolerability relative to acetylcholine esterase inhibitors. 5-HT4 receptor agonists also have antidepressant like properties (Expert Review of Neurotherapeutics, 2007, 7, 1357-1374; Experimental Neurology, 2007, 203(1), 274-278; Neuroscience & Medicine, 2011, 2, 87-92; Schizophrenia Bulletin, 2007, 33 (5), 1100-1119).

1-Isopropyl-3-{5-[1-(3-methoxypropyl) piperidin-4-yl]-[1,3,4]oxadiazol-2-yl}-1H-indazole oxalate of formula (I) is a promising pharmaceutical agent, which is a potent, selective and orally bioavailable 5-$HT_4$ receptor partial agonist intended for both disease modifying and symptomatic treatment of Alzheimer's disease and other disorders of memory and cognition like Attention deficit hyperactivity, Parkinson's and Schizophrenia. In addition to the pro-cognitive effects, the compound also demonstrated dose dependent antidepressant like effects in the mouse forced swim test. 1-Isopropyl-3-{5-[1-(3-methoxypropyl) piperidin-4-yl]-[1,3,4]oxadiazol-2-yl}-1H-indazole oxalate and its synthesis is disclosed by Ramakrishna et al. in WO2013042135.

At present, 1-Isopropyl-3-{5-[1-(3-methoxypropyl) piperidin-4-yl]-[1,3,4]oxadiazol-2-yl}-1H-indazole oxalate of formula (I) has completed preclinical studies and is ready to enter human clinical trials. The demand for 1-Isopropyl-3-{5-[1-(3-methoxypropyl) piperidin-4-yl]-[1,3,4]oxadiazol-2-yl}-1H-indazole oxalate of formula (I) as a drug substance would be increased substantially with the advent of its human clinical trials. The future need for much larger amounts is projected due to the intended commercialization of 1-Isopropyl-3-{5-[1-(3-methoxypropyl) piperidin-4-yl]-[1,3,4]oxadiazol-2-yl}-1H-indazole oxalate of formula (I).

For the person skilled in art, it is a well known fact that various parameters will change during the manufacturing of a compound on a large scale when compared to the synthetic procedures followed in laboratory. Therefore, there is a need to establish and optimize large scale manufacturing process. The process for the preparation of 1-Isopropyl-3-{5-[1-(3-methoxypropyl) piperidin-4-yl]-[1,3,4]oxadiazol-2-yl}-1H-indazole oxalate of formula (I) which was disclosed in WO2013042135 had been proved to be unsatisfactory for the large scale synthesis. Eventually, it is highly desirable to establish optimized manufacturing process for 1-Isopropyl-3-{5-[1-(3-methoxypropyl) piperidin-4-yl]-[1,3,4]oxadiazol-2-yl}-1H-indazole oxalate of formula (I) which is amenable to the large scale preparation.

SUMMARY OF THE INVENTION

The main object of the present invention is to provide a large scale, well optimized manufacturing process for 1-Isopropyl-3-{5-[1-(3-methoxypropyl) piperidin-4-yl]-[1,3,4] oxadiazol-2-yl}-1H-indazole oxalate of formula (I).

Another object of the invention is to provide a process to obtain substantially pure 1-Isopropyl-3-{5-[1-(3-methoxypropyl)piperidin-4-yl]-[1,3,4]oxadiazol-2-yl}-1H-indazole oxalate of formula (I).

Another object of this invention is to show the compatibility of the process to produce 1-Isopropyl-3-{5-[1-(3-methoxypropyl) piperidin-4-yl]-[1,3,4]oxadiazol-2-yl}-1H-indazole oxalate of formula (I) on a large scale using standard larger scale chemical process equipment.

Yet another object of this invention is to provide a commercial process for the production of 1-Isopropyl-3-{5-[1-(3-methoxypropyl) piperidin-4-yl]-[1,3,4]oxadiazol-2-yl}-1H-indazole oxalate of formula (I) on a larger scale.

DETAILED DESCRIPTION OF THE INVENTION

The large scale manufacturing process for preparation of 1-Isopropyl-3-{5-[1-(3-methoxypropyl) piperidin-4-yl]-[1,3,4]oxadiazol-2-yl}-1H-indazole oxalate of formula (I) of the present invention is illustrated in Scheme-1:

Scheme-1

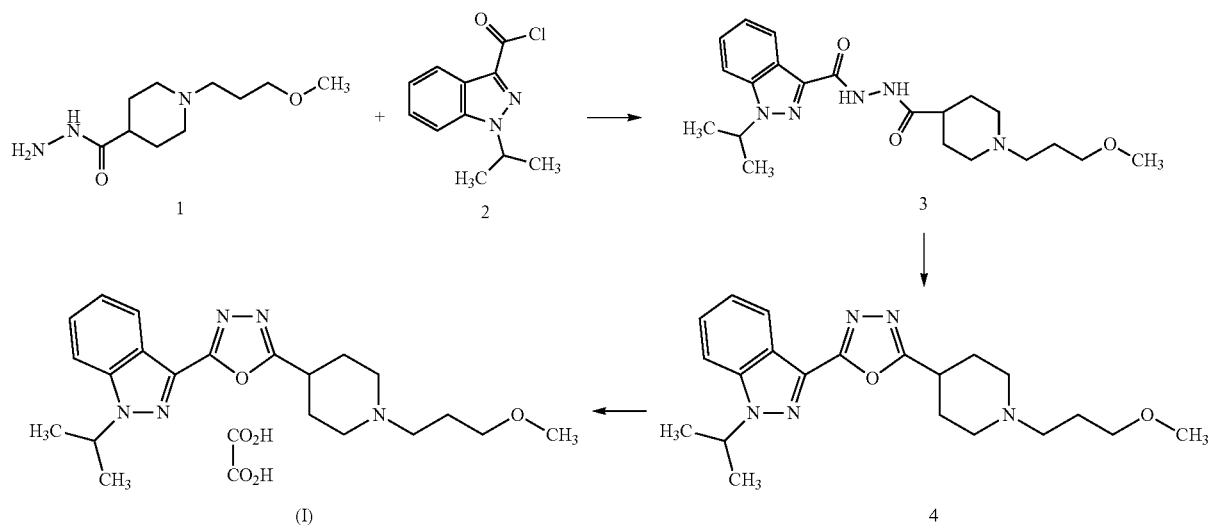

Step (i): Coupling of 1-(3-Methoxypropyl) piperidine-4-carboxylic acid hydrazide of formula 1 with 1-Isopropyl-1H-indazole-3-carbonyl chloride of formula 2 in presence of 1,2-dichloroethane to obtain N-[1-(3-Methoxypropyl) piperidine-4-carbonyl]N'-(1-isopropyl-1H-indazole-3-carbonyl) hydrazine of formula 3. The reaction temperature may range from 20° C. to 35° C., preferably at a temperature in the range from 25° C. to 30° C. The duration of the reaction may range from 1.5 hours to 2.5 hours, preferably for a period of 2 hours.

Step (ii): Cyclization of N-[1-(3-Methoxypropyl) piperidine-4-carbonyl]N'-(1-isopropyl-1H-indazole-3-carbonyl) hydrazine of formula 3 in presence of cyclizing agents such as phosphorousoxychloride, cyanuric chloride or thionyl chloride preferably thionyl chloride in solvents such as dichloromethane, 1,2-dichloroethane or chlorobenzene preferably 1,2-dichloroethane to obtain 1-isopropyl-3-{5-[1-(3-methoxypropyl) piperidin-4-yl]-[1,3,4]oxadiazol-2-yl}-1H-indazole of formula 4. The reaction temperature may range from 60° C. to 95° C., preferably at a temperature in the range from 70° C. to 85° C. The duration of the reaction may range from 8 hours to 10 hours, preferably for a period of 9 hours.

Step (iii): Purification of 1-Isopropyl-3-{5-[1-(3-methoxypropyl) piperidin-4-yl]-[1,3,4]oxadiazol-2-yl}-1H-indazole of formula 4 using mixture of acetic acid and water, preferably in the ratio of 1:9. The reaction temperature may range from 20° C. to 35° C., preferably at a temperature in the range from 25° C. to 30° C.

Step (iv): Reacting 1-Isopropyl-3-{5-[1-(3-methoxypropyl) piperidin-4-yl]-[1,3,4]oxadiazol-2-yl}-1H-indazole of formula 4 with oxalic acid in presence of isopropanol to obtain 1-Isopropyl-3-{5-[1-(3-methoxypropyl) piperidin-4-yl]-[1,3,4]oxadiazol-2-yl}-1H-indazole oxalate of formula (I). The reaction temperature may range from 20° C. to 35° C., preferably at a temperature in the range from 25° C. to 30° C. The duration of the reaction may range from 1 hour to 4 hours, preferably for a period of 2 hours.

Step (v): recrystallization of compound of formula (I) using a mixture of isopropanol and water, preferably in the ratio of 5:1. The reaction temperature may range from 70° C. to 80° C., preferably at a temperature in the range from 74° C. to 78° C. The duration of the reaction may range from 15 hours to 17 hours, preferably for a period of 16 hours.

The details of the invention are given in examples provided below.

Preparation 1: Preparation of
1-Isopropyl-1H-indazole-3-carboxylic acid

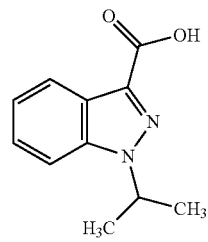

To a stirred solution of dimethylformamide (DMF) (50 L) at 25° C. to 30° C. under nitrogen atmosphere, sodium tert-butoxide (6.0 Kg, 62.43 mols) was added over a period of 15 minutes. The reaction mixture was stirred for 10 minutes after which it was cooled to 0° C. to 5° C. A solution of indazole-3-carboxylic acid (4.0 Kg, 24.67 mols) in DMF (50 L) was added slowly into the reactor over a period of 45 minutes, maintaining the reaction mass temperature at 0° C. to 5° C. The cooling was removed and the reaction temperature was gradually raised to 25° C. to 30° C. over a period of 30 minutes. After stirring at this temperature for 1 hour the reaction mixture was cooled to 0° C. and isopropyl iodide (6.32 Kg, 37.18 mols) was added over a period of 30 minutes. The cooling was removed and the reaction temperature was allowed to rise to 25° C. to 30° C. After 17 hours of stirring, the HPLC analysis of the reaction mixture revealed ≤10% of indazole-7-carboxylic acid remaining. The reaction mass was diluted cautiously with water (200 L) and washed with ethylacetate (2×100 L). The resultant aqueous layer was acidified to 4.0-4.5 pH with aqueous hydrochloride solution (6.0 N, 21.5 L) and extracted with ethylacetate (2×144 L). The combined organic layer was washed with water (2×100 L), brine solution (200 L) and dried over anhydrous sodium sulfate (4.0 Kg). The filtered organic layer was subjected to solvent removal under reduced pressure (>500 mm of Mercury) at 50° C. to 60° C. to obtain a crude mass. The obtained crude mass was diluted with dichloromethane (DCM) (28.0 L) and was stirred for 15 minutes. The solids precipitated (un-reacted indazole-7-carboxylic acid) were filtered through nutsche filter and the filter bed was washed once with DCM (8.0 L). The combined filtrate was distilled under reduced pressure (>500 mm of Mercury) at 45° C. to 55° C. to obtain a crude mass which was stirred with ether (7.0 L) for 30 minutes and filtered through nutsche filter to obtain the wet solid which was dried further in vacuum oven under reduced pressure (>500 mm of Mercury) at 45° C. to 55° C. to obtain above titled compound (3.0 Kg) as an off-white crystalline powder.

Yield: 59.5%;
Purity: 99.86%;
IR (cm$^{-1}$): 2980, 1729, 1682, 1487, 1287, 1203, 1170, 1127, 1085, 754;
$^1$H-NMR (δ ppm, CDCl$_3$): 8.27 (d, J=8.1 Hz, 1H), 7.55 (d, J=8.4 Hz, 1H), 0.7.46 (t, J=7.6 Hz, 1H), 7.34 (t, J=7.4 Hz, 1H), 5.01-4.95 (m, 1H), 1.68 (d, J=6.65 Hz, 6H);
Mass (m/z): 205.1 (M+H)$^+$.

Preparation 2: Preparation of 1-(3-Methoxypropyl) piperidine-4-carboxylic acid hydrazide

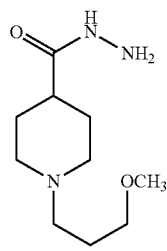 [SMILES: COCCCN1CCC(C(=O)NN)CC1]

Step (i): Preparation of Ethyl 1-(3-methoxypropyl) piperidine-4-carboxylate

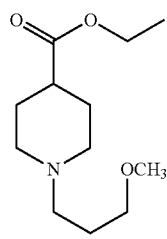 [SMILES: CCOC(=O)C1CCN(CCCOC)CC1]

To a stirred solution of acetonitrile (97.5 L) under nitrogen atmosphere at 25° C. to 30° C., ethyl isonipecotate (6.5 Kg, 41.35 mols) was added. The contents were stirred for 10 minutes after which potassium carbonate powder (7.35 Kg, 53.2 mols) and 1-Bromo-3-methoxy propane (6.89 Kg, 45.0 mols) were sequentially added. The reaction mixture was gradually heated to reflux (82° C.-85° C.) over a period of 30 minutes and was maintained at this temperature for 7 hours. At this time, the TLC revealed complete consumption of ethylisonipecotate. The volatiles were distilled off under reduced pressure (>500 mm of Mercury) at 50° C. to 60° C. The crude mass was cooled to 25° C. to 30° C. and was diluted with water (71.5 L) and DCM (136.5 L). After stirring the contents the two layers were separated. The organic layer was washed with water (71.5 L), dried over anhydrous sodium sulfate (6.5 Kg) and the volatiles were removed under reduced pressure (>500 mm of Mercury) at 50° C. to 55° C. to obtain the desired product (9.3 Kg) as pale yellow colored liquid.

Yield: 98%;
Purity: 98.8%;
IR (cm$^{-1}$): 2949, 1732, 1449, 1376, 1179, 1119, 1048;
$^1$H-NMR (δ ppm, CDCl3): 4.06 (q, J=7.1 Hz, 2H), 3.37-3.34 (t, J=6.4 Hz, 2H), 3.27 (s, 3H), 2.83-2.80 (m, 2H), 2.34 (t, J=7.5 Hz, 2H), 2.22-2.18 (m, 1H), 1.96-1.94 (m, 2H), 1.85-1.82 (m, 2H), 1.74-1.68 (m, 4H), 1.19 (t, J=7.04 Hz, 3H);
Mass (m/z): 230.4 (M+H)$^+$.

Step (ii): Preparation of 1-(3-Methoxypropyl) piperidine-4-carboxylic acid hydrazide

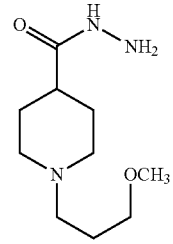 [SMILES: COCCCN1CCC(C(=O)NN)CC1]

To a stirred solution of methanol (38 L) under nitrogen atmosphere at 25° C. to 30° C., ethyl 1-(3-methoxypropyl) piperidine-4-carboxylate (5.0 Kg, 21.8 mols, obtained in above step) was added. After stirring the reaction mixture for 15 minutes, hydrazine hydrate (80% w/v, 4.1 Kg, 65.4 mols) was added over a period of 15 minutes. The reaction mixture was gradually heated to reflux (70° C.) over 30 minutes and continued stirring for 4 hours. Additional amount of hydrazine hydrate (80% w/v, 4.1 Kg, 65.4 mols) was added and the stirring continued for another 4 hours. Another installment of hydrazine hydrate (80% w/v, 4.1 Kg, 65.4 mols) was added and the stirring was continued for 16 hours at 70° C., upon which the Thin Layer Chromatography (TLC) reveals ≤5% of ester. The volatiles were distilled off under reduced pressure (>500 mm of Mercury) at 60° C. until syrupy mass appeared. After cooling syrypy mass to room temperature (25° C.-30° C.), it was diluted with DCM (38.0 L) and was stirred for 15 minutes. The observed two layers were then separated. The organic layer was dried over anhydrous sodium sulfate (5.0 Kg) and the solvent was evaporated under reduced pressure (>500 mm of Mercury) at 55° C. until dryness. The solid product which was separated was cooled to 25° C. to 30° C., diluted with hexanes (15.0 L) and the resultant slurry was filtered at nutsche filter. The filter bed was washed once with hexanes (15.0 L) and ethylacetate (2×10.0 L). The product cake was vacuum dried and the solid material thus separated was further dried in vacuum oven under reduced pressure (>500 mm of Mercury) at 50° C. for 6 hours to obtain the above titled compound (4.1 Kg) as an off-white crystalline powder.

Yield: 87%;
Purity: 99.79%;
IR (cm$^{-1}$): 3290, 3212, 2948, 2930, 1637, 1530, 1378, 1124, 1113, 986, 948, 789, 693;

$^1$H-NMR (δ ppm, CDCl$_3$): 6.83 (s, 1H), 3.86 (bs, 2H), 3.41 (t, J=6.4 Hz, 2H), 3.32 (s, 3H), 2.99-2.96 (m, 2H), 2.42 (t, J=7.44 Hz, 2H), 2.11-1.96 (m, 3H), 1.82-1.73 (m, 6H); Mass (m/z): 216.3 (M+H)$^+$.

Example 1: Preparation of 1-Isopropyl-3-{5-[1-(3-methoxypropyl) piperidin-4-yl]-[1,3,4]oxadiazol-2-yl}-1H-indazole oxalate Step (i): Preparation of N-[1-(3-Methoxypropyl) piperidine-4-carbonyl]N'-(1-isopropyl-1H-indazole-3-carbonyl) hydrazine

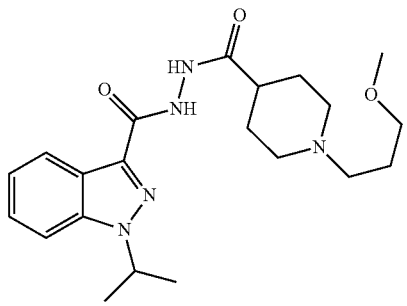 [SMILES: COCCCN1CCC(C(=O)NNC(=O)c2nn(C(C)C)c3ccccc23)CC1]

To a stirred solution of 1,2-dichloroethane (19.8 L) under nitrogen atmosphere at 25° C. to 30° C., 1-isopropyl-1H-indazole-3-carboxylic acid (3.0 Kg, 14.69 moles, obtained in preparation 1) was added and the reaction mixture was stirred for 15 minutes for complete dissolution. Thionyl chloride (3.6 Kg, 30.25 mols) was then added to the reaction mixture by maintaining its temperature below 30° C. over a period of 15 minutes. The reaction temperature was then gradually raised to 75° C. over a period of 30 minutes and was stirred for 2 hours at that temperature. The TLC revealed complete conversion of acid to acid chloride. The solvent 1,2-dichloroethane and excess thionyl chloride was removed under reduced pressure (>500 mm of Mercury) below 60° C. temperature. The obtained residual mass was cooled to 25° C. to 30° C., and diluted with DCM (15.6 L). The contents were further cooled to 0° C. to 5° C. A solution of 1-(3-Methoxypropyl) piperidine-4-carboxylic acid hydrazide (3.0 Kg, 13.94 mols, obtained in the preparation 2) in DCM (18.0 L) was added to the reaction mass over a period of 30 minutes. The reaction temperature was then gradually raised to 25° C. to 30° C. and the reaction mixture was stirred for 2 hours. The progress of the reaction was monitored by TLC which showed absence of hydrazide (≤1.0%). The reaction mixture was then diluted with water (30.0 L), stirred for 15 minutes and the two layers were separated. The aqueous layer was washed with DCM (1×30.0 L), cooled to 0° C. to 5° C. and cautiously basified to pH 7.6 with aqueous sodium bicarbonate solution (10% w/v, 46.5 L). The basified aqueous layer was then extracted with DCM (2×30.0 L). The combined organic layer was dried over anhydrous sodium sulfate (6.0 Kg) and the solvent was removed under reduced pressure (>500 mm of Mercury) below 55° C. The residue was then cooled to 25° C.-30° C. and diluted with solvent hexane (9.0 L). The slurry, thus obtained, was centrifuged at room temperature under nitrogen atmosphere and the wet product cake was washed with hexanes (6.0 L). The wet product was then dried in oven at 55° C.-60° C. until loss on drying was <1.0% to obtain the above titled compound (4.4 Kg) as an off white crystalline powder.

Yield: 74.5%;
Purity: 98.75%;
IR (cm$^{-1}$): 3506, 3233, 2943, 1703, 1637, 1523, 1487, 1195, 1116, 750;
$^1$H-NMR (δ ppm, CDCl$_3$): 9.35 (bs, 1H), 8.70 (bs, 1H), 8.30 (d, J=8.1 Hz, 1H), 7.48 (d, J=8.4 Hz, 1H), 7.42 (t, J=8.2 Hz, 1H), 7.29 (t, J=7.6 Hz, 1H), 4.90-4.85 (m, 1H), 3.40 (t, J=6.4 Hz, 2H), 3.33 (s, 3H), 2.94-2.85 (m, 2H), 2.39-2.31 (m, 3H), 1.92-1.88 (m, 4H), 1.76-1.65 (m, 4H), 1.59 (d, J=6.6 Hz, 6H);
Mass (m/z): 402.2 (M+H)$^+$.

Step (ii): Preparation of 1-Isopropyl-3-{5-[1-(3-methoxypropyl) piperidin-4-yl]-[1,3,4]oxadiazol-2-yl}-1H-indazole

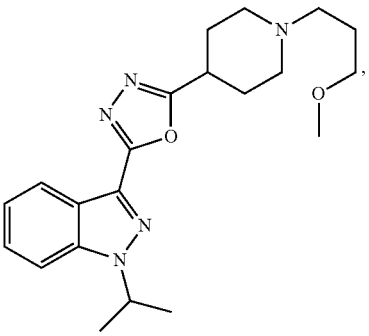 [SMILES: COCCCN1CCC(c2nnc(-c3nn(C(C)C)c4ccccc34)o2)CC1]

To a stirred solution of 1,2-dichloroethane (60 L) under nitrogen atmosphere at 25° C. to 30° C., N-[1-(3-methoxypropyl) piperidine-4-carbonyl]N'-(1-isopropyl-1H-indazole-3-carbonyl) hydrazine (3.0 Kg, 7.47 mols, obtained in above step) was added and the contents were stirred for 15 minutes after which, thionyl chloride (1.77 Kg, 15.0 mots) was added over 15 minutes time. The reaction mixture temperature was then gradually raised to 79° C.-83° C. over a period of 30 minutes at which the reaction mixture starts refluxing. Upon completion of 9 hours, the reaction mass showed complete consumption of starting material when checked by TLC. The excess thionyl chloride and solvent 1,2-dichloroethane were distilled off under reduced pressure (>500 mm of Mercury) below 60° C. The reaction mass was cooled to 25° C.-30° C., diluted with water (39.0 L) and solvent ether (19.5 L). The resulting mass was stirred for 15 minutes and the two layers were separated. The pH of the aqueous layer was adjusted to 9-10 by adding an aqueous solution of sodium hydroxide (2.5N, 3.0 L). The basified aqueous layer was then extracted with DCM (2×54.0 L). The combined organic layer was washed with cold (5° C.-10° C.) aqueous sodium hydroxide solution (0.6 N, 54.0 L), dried over anhydrous sodium sulfate (6.0 Kg) and the solvent was removed under reduced pressure (>500 mm of Mercury) below 55° C., which yielded above titled compound (2.6 Kg) as brown colored syrupy mass.

Yield: 90.5%;
Purity: 99.3%;
IR (cm$^{-1}$): 3054, 2946, 2808, 1599, 1563, 1462, 1389, 1211, 1120, 1069, 999, 749;
$^1$H-NMR (δ ppm, CDCl$_3$): 8.34 (d, J=8.12 Hz, 1H), 7.53 (d, J=8.44 Hz, 1H), 7.45 (t, J=7.58 Hz, 1H), 7.32 (t, J=7.44

Hz, 1H), 4.98-4.93 (m, 1H), 3.44 (t, J=6.44 Hz, 2H), 3.03-3.00 (m, 3H), 3.34 (s, 3H), 2.46 (t, J=7.54 Hz, 2H), 2.20-2.02 (m, 6H), 1.80 (t, J=7.27 Hz, 2H), 1.66 (d, J=6.72 Hz, 6H);

Mass (m/z): 384.3 (M+H)$^+$.

Step (iii): Purification of 1-Isopropyl-3-{5-[1-(3-methoxypropyl) piperidin-4-yl]-[1,3,4]oxadiazol-2-yl}-1H-indazole The above obtained crude step (ii) product was dissolved in a stirring aqueous acetic acid solution (10% w/v, 26.0 L) and washed with ethylacetate (2×26.0 L). The resultant aqueous layer pH was adjusted to 9.0-10.0 by adding an aqueous sodium hydroxide solution (0.5N, 52.0 L). The basified aqueous layer was extracted with solvent ether (2×26.0 L) and the combined organic layer was dried over anhydrous sodium sulfate (3.0 Kg). The volatiles were removed under reduced pressure (>500 mm of Mercury) below 55° C. to obtain a brown colored syrupy mass (2.19 Kg).

Yield: 84%;
Purity: 99.72%;
IR (cm$^{-1}$): 3054, 2978, 2946, 2808, 2772, 1599, 1563, 1462, 1389, 1194, 1177, 1120, 1069, 999, 749;
$^1$H-NMR (δ ppm, CDCl$_3$): 8.34 (d, J=8.12 Hz, 1H), 7.53 (d, J=8.44 Hz, 1H), 7.45 (t, J=7.58 Hz, 1H), 7.32 (t, J=7.44 Hz, 1H), 4.98-4.93 (m, 1H), 3.44 (t, J=6.44 Hz, 2H), 3.03-3.00 (m, 3H), 3.34 (s, 3H), 2.46 (t, J=7.54 Hz, 2H), 2.20-2.02 (m, 6H), 1.80 (t, J=7.27 Hz, 2H), 1.66 (d, J=6.72 Hz, 6H);

Mass (m/z): 384.4 (M+H)$^+$.

Step (iv): Preparation of 1-Isopropyl-3-{5-[1-(3-methoxypropyl) piperidin-4-yl]-[1,3,4]oxadiazol-2-yl}-1H-indazole oxalate To a stirred solution of isopropanol (60.8 L) under nitrogen atmosphere at 25° C.-30° C., 1-isopropyl-3-({5-[1-(3-methoxypropyl) piperidin-4-yl]-[1,3,4]oxadiazol-2-yl}-1H-indazole (6.08 Kg, 15.86 mols, obtained in step (iii) was added, followed by oxalic acid (1.46 Kg, 16.2 mols) addition. The reaction mixture was stirred for 2 hours and solid product that is precipitated was filtered through nutsche filter under nitrogen atmosphere. The wet product bed was washed with isopropanol (10.0 L) and solvent ether (60.8 L) to obtain a technical grade product.

IR (cm$^{-1}$): 3437, 2975, 2932, 2890, 1703, 1604, 1564, 1458, 1391, 1281, 1217, 1192, 1114, 992, 750;
$^1$H-NMR (δ ppm, DMSO-d$_6$): 10.72, (bs, 2H), 8.16 (d, J=8.1 Hz, 1H), 7.85 (d, J=8.5 Hz, 1H), 7.51 (t, J=7.4 Hz, 1H), 7.35 (t, J=7.7 Hz, 1H), 5.20-5.07 (m, 1H), 3.55-3.43 (m, 3H), 3.36 (t, J=5.9 Hz, 2H), 3.21 (s, 3H), 3.18-2.98 (m, 4H), 2.40-2.30 (m, 2H), 2.26-2.12 (m, 2H), 1.96-1.85 (m, 2H), 1.53 (d, J=6.6 Hz, 6H);

Mass (m/z): 384.4 (M+H)$^+$.

Step (v): Recrystallization of 1-Isopropyl-3-{5-[1-(3-methoxypropyl) piperidin-4-yl]-[1,3,4]oxadiazol-2-yl}-1H-indazole oxalate The above obtained product was suspended in a mixture of isopropanol (35.26 L) and water (7.3 L) and refluxed (76° C.) for 4 hours until complete dissolution. The homogenous solution thus obtained was gradually cooled to 25° C.-30° C. and maintained at this temperature under slow stirring for 16 hours. The precipitated oxalate salt was centrifuged under nitrogen atmosphere. The product cake was washed with isopropanol (15.0 L) and ether (60.8 L). The suction dried product was then dried in vacuum oven at 25° C.-30° C. for 2 hours and at 65° C. for 1 hour to obtain above titled compound (4.24 Kg) as light cream colored crystalline material.

Yield: 60%;
Purity: 99.92%;
Salt content (oxalate salt): 20.37%;
Heavy metals: <20 ppm;
IR (cm$^{-1}$): 3437, 2975, 2932, 2890, 1703, 1604, 1564, 1458, 1391, 1281, 1217, 1192, 1114, 992, 750;
$^1$H-NMR (δ ppm, DMSO-d$_6$): 10.72, (bs, 2H), 8.16 (d, J=8.1 Hz, 1H), 7.85 (d, J=8.5 Hz, 1H), 7.51 (t, J=7.4 Hz, 1H), 7.35 (t, J=7.7 Hz, 1H), 5.20-5.07 (m, 1H), 3.55-3.43 (m, 3H), 3.36 (t, J=5.9 Hz, 2H), 3.21 (s, 3H), 3.18-2.98 (m, 4H), 2.40-2.30 (m, 2H), 2.26-2.12 (m, 2H), 1.96-1.85 (m, 2H), 1.53 (d, J=6.6 Hz, 6H);

Mass (m/z): 384.4 (M+H)$^+$.

Advantages of the Invention

1. The current process is very simple and starts from the commercially and readily available starting material which makes the process economical and industrially viable.

2. The current process is devoid of silica gel column purifications which otherwise is not feasible for large scale synthesis.

3. The current process avoided the use of highly corrosive, hazardous and toxic phosphorous oxy chloride, which avoided laborious work up procedures for its removal, which makes the process cheaper, simple and safe.

4. The final compound obtained in current process is >99.9% HPLC purity.

We claim:

1. A process for large scale production of 1-Isopropyl-3-{5-[1-(3-methoxypropyl)piperidin-4-yl]-[1,3,4]oxadiazol-2-yl}-1H-indazole oxalate of formula (I),

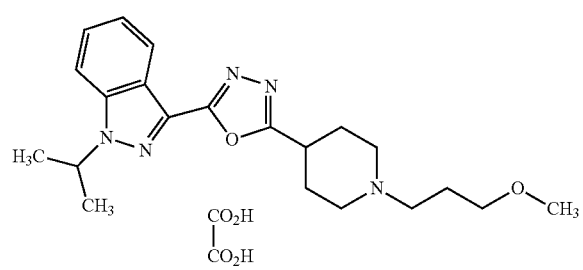

(I)

the process comprising the steps of:

Step (i): coupling of 1-(3-Methoxypropyl) piperidine-4-carboxylic acid hydrazide of formula 1 with 1-Isopropyl-1H-indazole-3-carbonyl chloride of formula 2

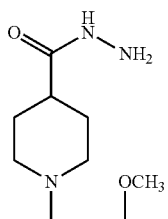

1

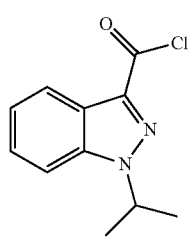

2 in presence of dichloroethane at a temperature in the range of 20° C. to 35° C. for a period of 1.5 hours to 2.5 hours to obtain N-[1-(3-Methoxypropyl) piperidine-4-carbonyl]N'-(1-isopropyl-1H-indazole-3-carbonyl) hydrazine of formula 3;

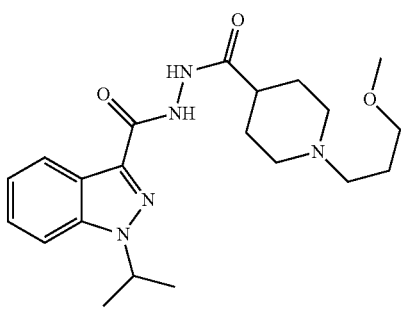

3

Step (ii): cyclizing N-[1-(3-Methoxypropyl) piperidine-4-carbonyl]N'-(1-isopropyl-1H-indazole-3-carbonyl) hydrazine of formula 3 in presence of thionyl chloride in solvent selected from dichloromethane, 1,2-dichloroethane and chlorobenzene at a temperature in the range of 60° C. to 95° C. for a period of 8 hours to 10 hours to obtain 1-isopropyl-3-{5-[1-(3-methoxypropyl) piperidin-4-yl]-[1,3,4]oxadiazol-2-yl}-1H-indazole of formula 4;

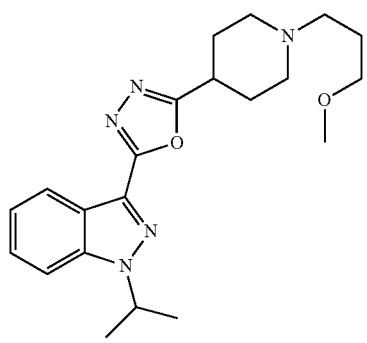

4

Step (iii): purifying 1-isopropyl-3-{5-[1-(3-methoxypropyl) piperidin-4-yl]-[1,3,4]oxadiazol-2-yl}-1H-indazole of formula 4 using mixture of acetic acid and water at a temperature in the range of 20° C. to 35° C.;

Step (iv): reacting 1-isopropyl-3-{5-[1-(3-methoxypropyl) piperidin-4-yl]-[1,3,4]oxadiazol-2-yl}-1H-indazole of formula 4 with oxalic acid in presence of isopropanol at a temperature in the range of 20° C. to 35° C. for a period of 1 hour to 4 hours to obtain 1-Isopropyl-3-{5-[1-(3-methoxypropyl) piperidin-4-yl]-[1,3,4]oxadiazol-2-yl}-1H-indazole oxalate of formula (I);

Step (v): recrystallizing compound of formula (I) using a mixture of isopropanol and water at a temperature range of 70° C. to 80° C. for a period of 15 hours to 17 hours

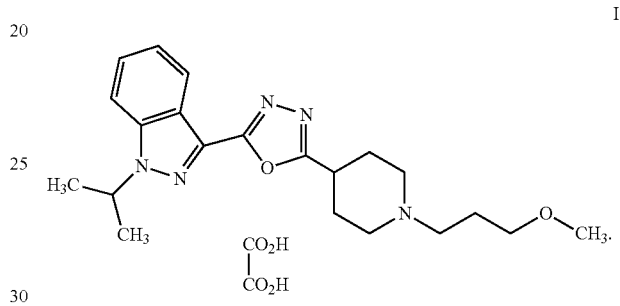

I

2. The process as claimed in claim 1, wherein the temperature used in Step (i) is 25° C. to 30° C.

3. The process as claimed in claim 1, wherein the duration of reaction in Step (i) is 2 hours.

4. The process as claimed in claim 1, wherein the temperature used in Step (ii) is 70° C. to 85° C.

5. The process as claimed in claim 1, wherein the duration of reaction in Step (ii) is 9 hours.

6. The process as claimed in claim 1, wherein the ratio of acetic acid and water in Step (iii) is 1:9.

7. The process as claimed in claim 1, wherein the temperature used in Step (iii) is 25° C. to 30° C.

8. The process as claimed in claim 1, wherein the temperature used in Step (iv) is 25° C. to 30° C.

9. The process as claimed in claim 1, wherein the duration of reaction in Step (iv) is 2 hours.

10. The process as claimed in claim 1, wherein the temperature used in Step (v) is 74° C. to 78° C.

11. The process as claimed in claim 1, wherein the duration of reaction in Step (v) is 16 hours.

12. The process as claimed in claim 1, wherein the ratio of isopropanol and water in Step (v) is 5:1.

13. The process as claimed in claim 1, wherein the purity of 1-Isopropyl-3-{5-[1-(3-methoxypropyl) piperidin-4-yl]-[1,3,4]oxadiazol-2-yl}-1H-indazole oxalate of formula (I) is >99.9% pure.

14. A process for large scale production of N-[1-(3-Methoxypropyl) piperidine-4-carbonyl]N'-(1-isopropyl-1H-indazole-3-carbonyl) hydrazine of formula 3, the process comprising the step of:

Step (i): coupling of 1-(3-Methoxypropyl) piperidine-4-carboxylic acid hydrazide of formula 1 with 1-Isopropyl-1H-indazole-3-carbonyl chloride of formula 2

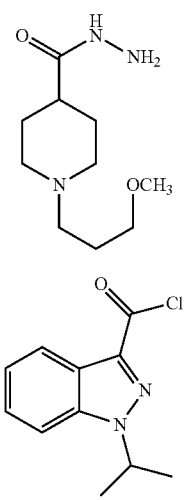
1
2
in presence of dichloroethane at a temperature in the range of 20° C. to 35° C. for a period of 1.5 hours to 2.5 hours to obtain N-[1-(3-Methoxypropyl) piperidine-4-carbonyl]N'-(1-isopropyl-1H-indazole-3-carbonyl) hydrazine of formula 3
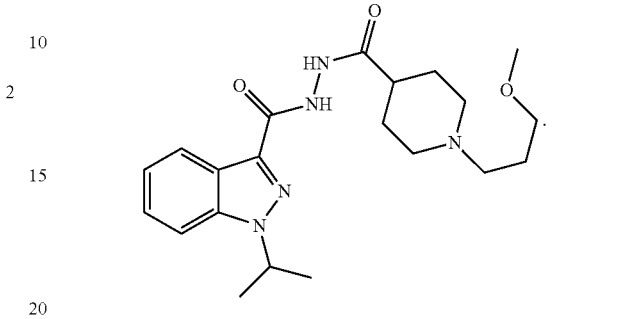
3
* * * * *